United States Patent [19]

Singh et al.

[11] Patent Number: 4,474,693

[45] Date of Patent: Oct. 2, 1984

[54] ACE INHIBITORS PRODUCED FROM *NOCARDIA ORIENTALIS*

[75] Inventors: Pushpa Singh, Piscataway; Karen Bush, Kingston; Dorothy S. Slusarchyk, Belle Mead, all of N.J.

[73] Assignee: E. R. Squibb & Sons, Inc., Princeton, N.J.

[21] Appl. No.: 547,151

[22] Filed: Oct. 31, 1983

[51] Int. Cl.$^3$ .................. C07C 103/52; C07G 7/00
[52] U.S. Cl. ...................... 260/112.5 R; 260/112 R
[58] Field of Search ................. 260/112.5 R, 112 R

[56] References Cited

U.S. PATENT DOCUMENTS 4,317,771  3/1982  Shiba et al. ............... 260/112.5 R Primary Examiner—Delbert R. Phillips
Attorney, Agent, or Firm—Lawrence S. Levinson; Donald J. Barrack

[57] ABSTRACT $N^2$-[N-(N-acetylmuramoyl)-L-alanyl]-N-(5,6-diamino-1-carboxyl-6-oxohexyl)-D-α-glutamine, $N^2$-[N-(N-acetylmuramoyl)-L-alanyl]-N-[5,6-diamino-1-[[1-[(1-carboxyethyl)carbamoyl]ethyl]carbamoyl]-6-oxohexyl]-D-α-glutamine and EM5556C are obtained as a mixture by cultivating a strain of the microorganism *Nocardia orientalis* A.T.C.C. No. 39444.

4 Claims, 2 Drawing Figures

INFRARED SPECTRUM OF EM5556C AS THE MONOSODIUM SALT IN POTASSIUM BROMIDE

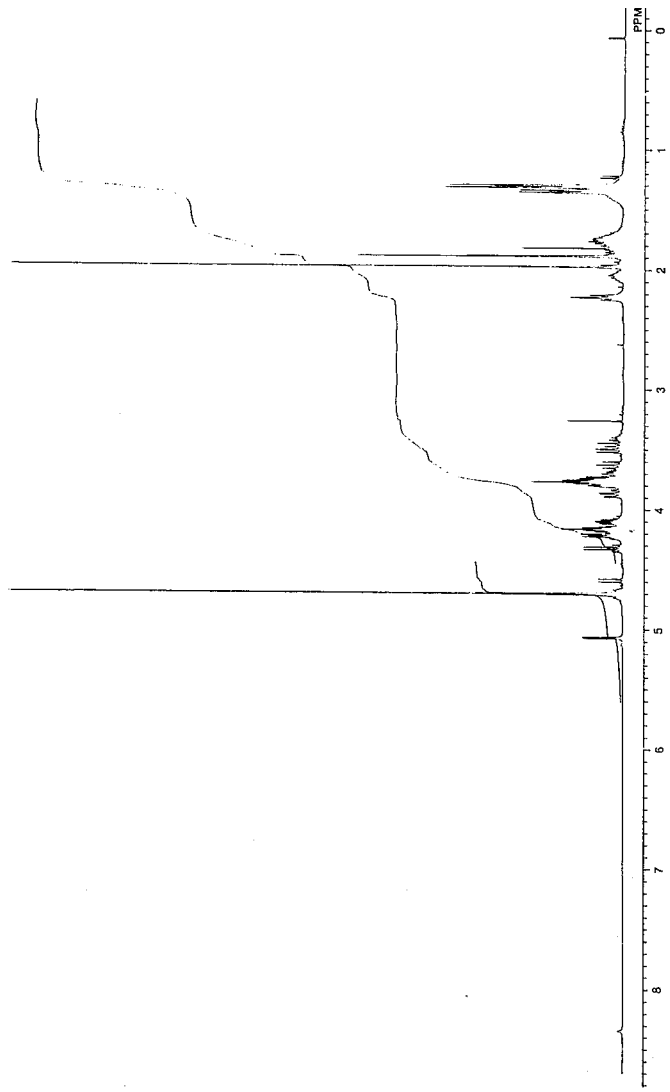

ACE INHIBITORS PRODUCED FROM *NOCARDIA ORIENTALIS*

BACKGROUND OF THE INVENTION

U.S. Pat. No. 4,186,194, issued Jan. 29, 1980, discloses water soluble agents which are said to be immunological adjuvants for stimulating in the host the immune response to various antigens. The compounds comprise an acetyl or glycolyl muramic acid group, and a short peptide chain linked thereto, the first amino acid of the peptide chain being alanine, serine or glycine and the second amino acid of the peptide chain being glutamic acid or aspartic acid.

SUMMARY OF THE INVENTION

A mixture of at least four components, designated EM5556, is obtained by cultivating a strain of the microorganism *Nocardia orientalis* which has been deposited in the American Type Culture Collection as A.T.C.C. No. 39444. EM5556 is a mixture of at least four components, two of which have been characterized as N²-[N-(N-acetylmuramoyl)-L-alanyl]-N-(5,6-diamino-1-carboxy-6-oxohexyl)-Dα-glutamine glutamine which has the structural formula

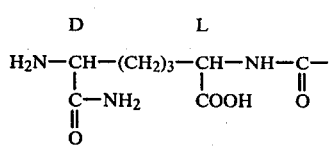

Reduction of N²-[N-(N-acetylmuramoyl)-L-alanyl]-N-(5,6-diamino-1carboxy-6-oxohexyl)-D-α-glutamine yields 2-(acetylamino)-3-O-[(R)-2-[(S)-2-[[(R)-1-carboxy-4-[[(1S,5R)-5,6-diamino-1-carboxy-6-oxohexyl]amino]-4-oxobutyl]amino]-1-methyl-2-oxoethyl]amino]-1-methyl-2-oxoethyl]-2-desoxy-D-glucitol, which has the structural formula

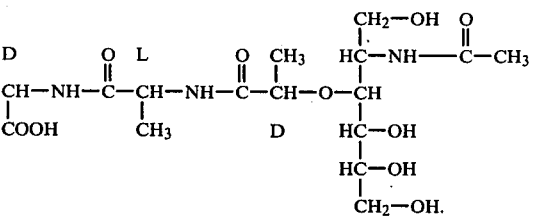

The mixture EM5556, the three components which have been isolated in pure form, and 2-(acetylamino)-3-O-[(R)-2-[(S)-2-[[(R)-1-carboxy-4-[[(1S,5R)-5,6-diamino-1-carboxy-6-oxohexyl]amino]-4-oxobutyl]amino]-1-methyl-2-oxoethyl]amino]-1-methyl-2-oxoethyl]-2-desoxy-D-desoxy-D-glucitol are hypotensive agents. They inhibit the conversion of the decapeptide angiotensin I to angiotensin II and therefore, are useful in reducing or relieving angiotensin related hypertension. The action of the enzyme renin on angiotensinogen, a pseduoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→ angiotensin I→(ACE)→ angiotensin II sequence by inhibiting angiotensin converting enzyme and reducing or eliminating the formation of the pressor substance angiotensin II. Thus by the administration of a composition containing one (or a combinaand N²-[N-(N-acetylmuramoyl)-L-alanyl]-N-[5.6-diamino-1-[[1-[(1-carboxyethyl))carbamoyl]ethyl]-carbamol]-6-oxohexyl]-D-α-glutamine which has the structural formula

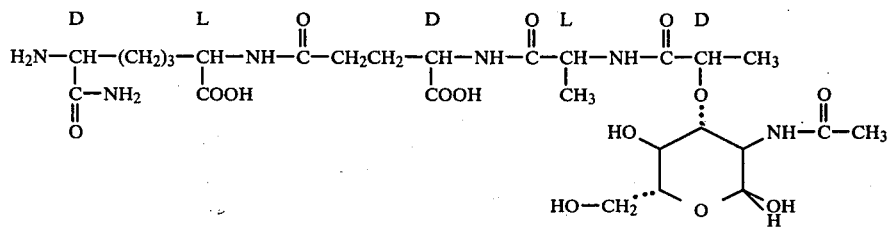

The third component has been designated EM5556C and is known to be a muramylpentapeptide containing N-acetylmuramic acid, alanine, glutamic acid, serine and diaminopimelic acid in a 1:2:1:1:1 ratio based on the NMR spectrum. The fouth component has not been isolated in pure form.

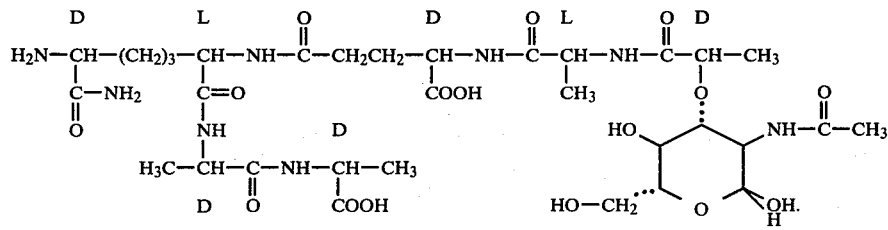

tion) of the compounds of this invention, angiotensin dependent hypertension in a species of mammal (e.g., humans) suffering therefrom is alleviated. A single dose, or preferably two to four divided daily doses, provided on a basis of about 0.1 to 100 milligrams per kilogram of body weight per day, preferably about 1 to 15 milligrams per kilogram of body weight per day is appropriate to reduce blood pressure. The substance is administered parenterally.

DESCRIPTION OF THE DRAWINGS

FIG. 2 shows the 400 MHz $^1$H NMR spectrum of EM5556C as the monosodium salt in deuterated water.

DETAILED DESCRIPTION OF THE INVENTION

The Microorganism

Figure 1:
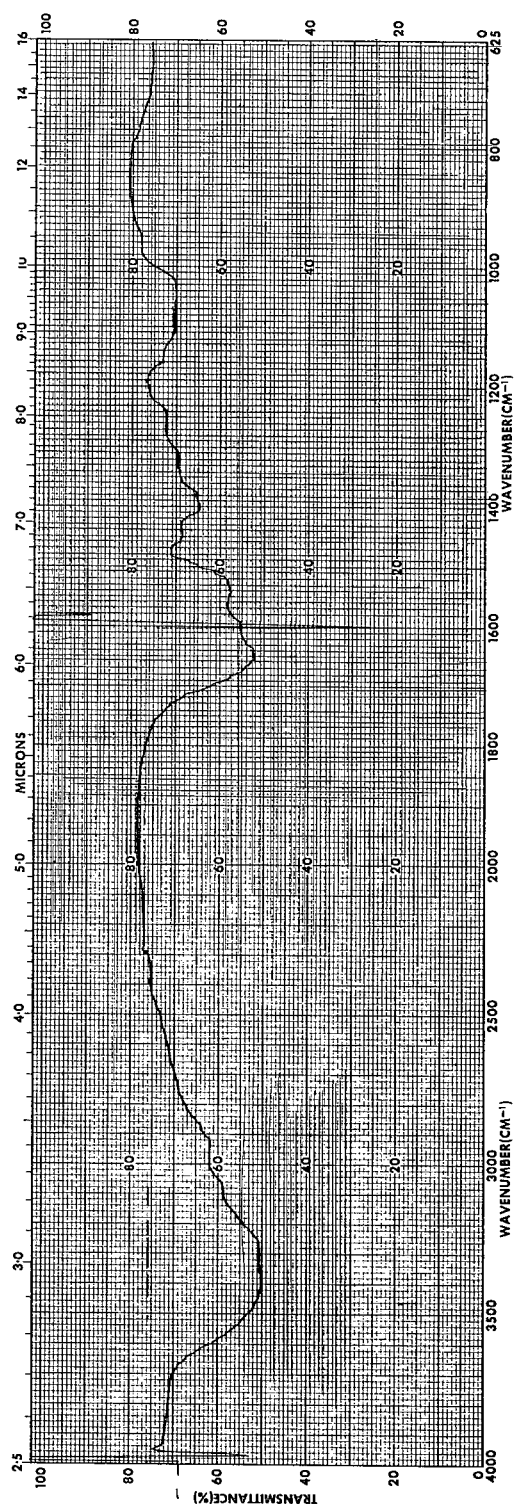
FIG. 1 shows the infrared spectrum of EM5556C as the monosodium salt in potassium bromide.

The microorganism used for the production of EM5556 is a strain of *Nocardia orientalis* isolated from the soil. A subculture of the organism may be obtained from the American Type Culture Collection, Rockville, Md. Its accession number in the repository is A.T.C.C. No. 39444.

The characteristics of *Nocardia orientalis* A.T.C.C. No. 39444 are:

The organism producing EM5556 is identified as a strain of *Nocardia orientalis* found to be identical with the type strain of this species ISP-5040 which is A.T.C.C. No. 19795.

The vegetative mycelium exhibits characteristic fragmentation, and a rudimentary aerial mycelium is produced. Cell wall acid hydrolysates contain meso-DAP, with galactose and arabinose as the major sugar components. This provides the basis for placement in the genus Nocardia.

The organism produces positive test responses with respect to the following biochemical characteristics:

(1) decomposition of casein, testosterone, tyrosine and xanthine;

(2) acid production from adonitol, cellobiose, meso-erythritol, lactose, maltose, α-methyl-D-glucoside;

(3) urease.

The following characteristics give negative responses:

(1) decomposition to adenine;

(2) acid from melezitose;

(3) resistance to lysozyme and rifampin.

All tests were run according to the methods described in the following references:

(1) Gordon, R. E., and Mihm, J. M. (1957) & J. Bacteriol. 73:15–27

(2) Gordon, R. E., et al. (1978) J. Gen. Microbiol. 109:69–79

(3) Goodfellow, M., Schaal, K. P. (1979) Identification Methods for Nocardia, Actinomadura and Rhodococcus, pp. 261–276. In: Loveluck, D. W., Skinner, F. A. (eds.), Identification Methods for Microbiologists, 2nd ed. Soc. App. Bacteriol. Tech. Ser. London: Academic Press.

For isolating the organism, a portion of the soil sample (obtained in Hamilton Township, N.J.) is stamped onto an agar of the following composition:

| | |
|---|---|
| Glycerol | 12.6 ml |
| Citric Acid | 1.2 gm |
| (NH$_4$)$_2$HPO$_4$ | 0.4 gm |
| KCl | 0.08 gm |
| MgCl$_2$.6H$_2$O | 0.418 gm |
| MnCl$_2$.4H$_2$O | 0.036 gm |
| FeSO$_4$.7H$_2$O | 0.023 gm |
| ZnCl$_2$.6H$_2$O | 0.021 gm |
| CoCl$_2$.6H$_2$O | 0.004 gm |
| Agar | 15.0 gm |

The medium is adjusted to pH about 7.2 and sterilized in an autoclave at 121° C. for 30 minutes. After 3 to 5 days incubation at 25° C., the colonies of *Nocardia orientalis* A.T.C.C. No. 39444 are isolated from the plated soil. The isolated colonies are picked off and maintained on an agar medium composed of:

| | |
|---|---|
| Oatmeal | 20 gm |
| Tomato paste | 20 gm |
| Agar | 15 gm |
| Tap water to | 1000 ml |

The medium is adjusted to pH about 7 and sterilized in an autoclave at 121° C. for 15 minutes.

Production of EM5556

*Nocardia orientalis* A.T.C.C. No. 39444 produces EM5556 which possesses angiotensin converting enzyme inhibitory activity. To form EM5556 according to the preferred methodology of this invention, *Nocardia orientalis* A.T.C.C. No. 39444 is grown at, or near, room temperature (25° C.) under submerged aerobic conditions in an aqueous nutrient medium containing an assimilable carbohydrate and nitrogen source. The fermentation is carried out until substantial activity is imparted to the medium, usually about 120 to 144 hours.

After the fermentation is complete, cells are removed by centrifugation and the broth supernate is adjusted to pH 3.0 (if needed) and loaded onto a column of Darco granular charcoal. Eluting with acetone-water (1:1) the active fractions are determined by assaying for ACE inhibition using a spectrophotometer with captopril as the positive standard and p-nitrobenzyloxycarbonyl-glycyl(S-4-nitrobenzo-2-oxa-1,3-diazole)-L-cysteinylglycine as the chromogenic substrate and partially purified rabbit lung ACE as enzyme (see A. V. Persson et al., A New Chromogenic Substrate for Angiotensin-Converting Enzyme, Analytical Biochemistry, 91:674 (1978)). The active fractions are purified by anion exchange chromatography.

The active components of EM5556 are separated by reverse phase chromatography on a column of MCI gel CHP20P (a styrene and divinylbenzene copolymer having a macroreticular structure) eluting with water followed by a linear gradient of 0–66% acetone-water. The major activity elutes with water and is fractionated on the basis of TLC and HPLC analysis.

The following examples further illustrate this invention.

EXAMPLE 1

The following is a detailed description of the fermentation of *Nocardia orientalis* A.T.C.C. No. 39444, and the isolation of the resulting product.

*Nocardia orientalis* A.T.C.C. No. 39444 was maintained on the following sterilized agar medium (A):

| | Grams |
|---|---|
| Oatmeal | 20 |
| Tomato paste | 20 |
| Agar | 15 |
| Tap water to | 1 Liter |

The pH was adjusted to 7.0 before sterilization at 121° C. for 15 minutes. A loopful of surface growth from an agar slant (Medium A) of *Nocardia orientalis* was used to inoculate each of eight 500 ml Erlenmeyer flasks containing 100 ml each of the following sterilized medium (B):

|  | Grams |
| --- | --- |
| Yeast extract | 4 |
| Malt extract | 10 |
| Dextrose | 4 |
| Distilled water to | 1 Liter |

The pH was adjusted to 7.3 before sterilization at 121° C. for 15 minutes. After inoculation, the flasks were then incubated at 25° C. on a rotary shaker (300 rpm: 2 inch stroke) for approximately 72 hours. After the appropriate incubation as described above, 3.0% (vol.-/vol.) transfers were made from the grown culture flasks to two hundred 500 ml Erlenmeyer flasks containing 100 ml each of the following sterilized medium (C):

|  | Grams |
| --- | --- |
| $(NH_4)_2SO_4$ | 2.64 |
| $K_2HPO_4$ | 4.3 |
| $KH_2PO_4$ | 2.38 |
| $MgSO_4.7H_2O$ | 1.0 |
| Glucose | 10.0 |
|  | (Sterilized separately) |
| Salt solution* | 1.0 ml/liter |
| Distilled $H_2O$ to | 1 Liter |

*Salt Solution
gm/100 ml distilled water: $CuSO_4.5H_2O$ - 0.64;
$FeSO_4.7H_2O$ - 0.11;
$MnCl_2.4H_2O$ - 0.79;
$ZnSO_4.7H_2O$ - 0.15

The pH was adjusted to 6.8–7.0 before sterilization of 121° C. for 15 minutes. After inoculation, the flasks were incubated at 25° C. on a rotary shaker (300 rpm: 2 each stroke) for approximately 120 hours. At this time the contents of the flasks were pooled and the broth was centrifuged yielding approximately 19 liters of supernatant broth; the cells were discarded.

The broth supernate (19 L, PH 3.0) was loaded onto a Darco granular charcoal** column (5×45cm) at a rate of 63 ml/minute. The column was washed with water (3 L) and then eluted with four 1 L-portions of acetone- water (1:1). The fractions were assayed for ACE inhibition using a spectrophotometer with captopril as the positive standard and o-nitrobenzyloxycarbonylglycyl (S-4-nitrobenzo-2-oxa-1.3-diazole)-L-cysteinylglycine as the chromogenic substrate and partially purified rabbit lung ACE as enzyme. The active fractions were combined (4 L) and concentrated in vacuo (9.97 g). The residue was dissolved in water (10 ml) and the pH of the solution was adjusted to 9.0 with 5N NaOH. The solution was applied to a column of BioRad AG1×2, OAc⁻*, 200–400 mesh (5×30 cm). The column was washed with five 120 ml portions of water and then eluted with a linear gradient prepared from water (3 L) and 0.25M pyridine-acetic acid, pH 5.1 (3 L). Fractions (25 ml) were collected, a small portion of each fraction was diluted with water (1:30 dilution) and assayed for ACE inhibition. The active fractions (123–144) were combined (525 ml) and concentrated in vacuo to give 1.2 g of a yellow solid which contained $N^2$-[N-(N-acetylmuramoyl)-L-alanyl]-N-(5,6-diamino-1-carboxy-6-oxohexyl)-D-α-glutamine, $N^2$-[N-(N-acetylmuramoyl)-L-alanyl]-N-[5,6-diamino-1-[[1-[(1-carboxyethyl)carbamoyl]ethyl]-carbamoyl]-6-oxohexyl]-D-α-glutamine and EM5556C.

**Darco granular charcoal (MCB Manufacturing Chemists, Inc., Gibbstown, N.J.)
*BioRad AG1×2, OAc⁻ (Bio-Rad Laboratories, Richmond, Calif.) is a strongly basic anion exchange resin with quaternary ammonium functional groups attached to the styrene divinylbenzene copolymer.

The 1.2 g of the yellow solid containing $N^2$-[N-(N-acetylmuramoyl)-L-alanyl]-N-(5,6-diamino-1-carboxy-6-oxohexyl)-D-α-glutamine, $N^2$-[N-(N-acetylmuramoyl)-L-alanyl]-N-[5,6-diamino-1-[[1-[(1-carboxyethyl) carbamoyl]ethyl]carbamoyl]-6-oxohexyl]-D-α-glutamine and EM5556C was dissolved in water (1 ml, pH 3.5) and applied to a reverse phase column of MCI gel CHP20P* (2.5×54cm). The column was eluted with water (600 ml, 7 ml fractions collected) followed by a linear gradient prepared from water (300 ml) and 66% acetone-water (300 ml, 8 ml fractions collected). Fractions were assayed for ACE inhibition using the methodology described above, and were combined on the basis of TLC (silica gel, ethyl acetate-butanol-acetic acid-water, 1:1:1:1, Rydon-visualization, system I) and HPLC analysis on a $C_{18}$ spherical packed column with Z-module** using 10% acetonitrile, 0.1% 1-heptanesulfonic acid, sodium salt, in water (isocratic, pH 2.1 with HCl, 1.5 ml/minute, 210 nm). Fractions 44–74 contained $N^2$-[N-(N-acetylmuramoyl)-L-alanyl]-N-(5,6-diamino-1-carboxy-6-oxohexyl)-D-α-glutamine by TLC ($r_f$=0.19, system I) and HPLC (Table 1) analysis, these were concentrated in vacuo to give 121 mg of $N^2$-[N-(N-acetylmuramoyl)-L-alanyl]-N-(5,6-diamino-1-carboxy -6-oxohexyl)-D-α-glutamine, the sodium salt, as a white powder.

*MCI gel CHP20P (Mitsubishi Chemical Industries, Ltd., Japan) is a styrene and divinylbenzene copolymer in a bead form having a macroreticular structure.
**Z-module TM (Waters Assoc.) is a radial compressor system. It is a self-contained manually operated unit into which a Radial-pak cartridge is inserted. The module utilizes a precision stainless steel chamber which fits tightly over the cartridge to cause uniform radial compression throughout the cartridge's packed bed.

Fractions 75–113 contained a mixture of the above $N^2$-[N-(N-acetylmuramoyl)-L-alanyl]-N-(5,6-diamino-1-carboxy -6-oxohexyl)-D-α-glutamine and EM5556C as shown by TLC ($r_f$=0.19 for $N^2$-[N-(N-acetyl-muramoyl)-L-alanyl]-N-(5.6-diamino-1-carboxy -6-oxohexyl)-D-α-glutamine and $r_f$=0.15 for EM5556C, system I) and HPLC (Table 1) analysis. These were combined and concentrated to dryness to give 145 mg of a residue consisting of $N^2$-[N-(N-acetylmuramoyl)-L-alanyl]-N-(5,6-diamino-1-carboxy -6-oxohexyl)-D-α-glutamine and EM5556C. This mixture was further purified as described below to give more of $N^2$-[N-(N-acetylmuramoyl)-L-alanyl]-N-(5,6diamino-1-carboxy-6-oxohexyl)-D-α-glutamine and EM5556C.

The residue (145 mg) obtained above was dissolved in water (0.7 ml, pH 3.5) and applied to a reverse phase column of MCI Gel CHP20P (2.5×50cm). The column was eluted with water (1.2 L, 8 ml fractions), and the fractions were assayed for ACE inhibition. The active fractions were fractionated on the basis of TLC (system I) and HPLC analysis. Fractions 30–84 contained $N^2$-[N-(acetylmuramoyl) -L-alanyl]-N-(5,6-diamino-1-carboxy-6-oxohexyl) -D-α-glutamine by TLC ($r_f$=0.19, system I) and HPLC (Table 1), these were combined and concentrated in vacuo to give 42.2 mg of $N^2$-[N-(N-acetylmuramoyl) -L-alanyl]-N-(5,6-diamino-1-carboxy-6-oxohexyl-D-α-glutamine, sodium salt, as a white powder. Fractions 130–145 contained EM5556C by TLC ($r_f$=0.15, system I) and HPLC (Table 1). These were combined and concentrated in vacuo to give 5.3 mg of EM5556C, sodium salt as a white powder.

The infrared spectrum of EM5556C as the monosodium salt in potassium bromide is shown in FIG. 1. The 400 MHz $^1$H-NMR spectrum of EM5556C as the monosodium salt in deuterium is shown in FIG. 2.

A mass spectrum of EM5556C was obtained by the fast atom bombardment (FAB) technique, which gave peaks at m/z 823 and 845 in the positive-ion mode, indicating a molecular weight of 822 and 844 for the free acid and the monosodium salt, respectively.

The elemental composition of EM5556C was obtained by high resolution FAB mass spectrometry. The observed mass for $C_{32}H_{55}N_8O_{17}$ (M+H)$^+$ was 823.373 (theory 823.368).

The 1.2 g of the yellow solid containing $N^2$[N-(N-acetylmuramoyl)-L-alanyl]-N-(5,6-diamino-1-carboxy-6-oxohexyl)-D-α-glutamine, $N^2$-[N-(N-acetylmuramoyl)-L-alanyl]-N-[5,6-diamino-1[[1-[(1-carboxyethyl)carbamoyl]ethyl]carbamoyl]-6-oxohexyl]-D-α-glutamine and EM5556C was dissolved in water (1 ml, the pH 3.5) and applied to a reverse phase column of MCI gel CHP20P (2.5×54cm). The column was eluted with water (600 ml, 7 ml fractions collected) followed by a linear gradient prepared from water (300 ml) and 66% acetone-water (300 ml, 8 ml fractions collected). Fractions were assayed for ACE inhibition. The major activity eluted with water which contained $N^2$-[N-(N-acetylmuramoyl-L-alanyl]-N-(5,6-diamino-1-carboxy-6-oxohexyl)-D-α-glutamine and EM5556C (described earlier).

A less active band was eluted with ~54% acetone-water (fractions 162-165); this contained $N^2$-[N-(N-acetylmuramoyl)-L-alanyl]-N-[5.6-diamino-1-[[1-[(1-carboxyethyl)carbamoyl]ethyl]carbamoyl]-6-oxohexyl]-D-α-glutamine by TLC ($r_f$=0.19, system I) and HPLC (Table 1) analysis. Fractions 162-165 were combined and concentrated in vacuo to give 410 mg of $N^2$-[N-(N-acetylmuramoyl)-L-alanyl]-N-[5,6-diamino-1-[[1-[(1-carboxyethyl)carbamoyl]ethyl]-carbamoyl]-6-oxohexyl]-D-α-glutamine, sodium salt, as a white powder.

TABLE 1

HPLC Retention Times of Components of EM5556

| Compound | Retention Time (Min.) | |
|---|---|---|
| | α-anomer | β-anomer |
| $N^2$—[N—(N—acetylmuramoyl)-L-alanyl]-N—(5,6-diamino-1-carboxy-6-oxohexyl)-D- | 6.2 | 6.9 |
| α-glutamine | | |
| $N^2$—[N—(N—acetylmuramoyl)-L-alanyl]-N—[5,6-diamino-1-[[1-[(1-carboxyethyl)carbomyl]ethyl]carbomyl]-6-oxohexyl]-D-α-glutamine | 9.7 | 11.9 |
| EM5556C | 8.5 | 10.0 |
| Conditions: | $C_{18}$ spherical packed column (8 mm × 10 cm) with Z-module using 10% acetonitrile, 0.1% 1-heptanesulfonic acid, sodium salt in water (isochratic, pH 2.1 with HCl), flow rate 1.5 ml/minute at 210 nm | |

EXAMPLE 2

2-(Acetylamino)-3-O-[(R)-2-[(S)-2-[[(R)-1-carboxy-4-[[(1S,5R)-5,6-diamino-1-carboxy-6-oxoethyl]amino]-4-oxobutyl]amino]-1-methyl-2-oxoethyl]-2-desoxy-D-glucitol.

A suspension of $N^2$-[N-(acetylmuramoyl)-L-alanyl]-N-(5,6-diamino-1-carboxy-6-oxohexyl)-D-α-glutamine (41.2 mg, 62 μmol) in a mixture of water (1 ml) and tetrahydrofuran (9 ml) was stirred with sodium borohydride (2.6 mg, 68 μmol) at room temperature for 15 minutes. The TLC analysis (silica, ethyl acetate:n-butanol:acetic acid:water, 1:1:1:1, Rydon-detection) showed that the reaction was incomplete. An additional 2 mg (52 μmol) of sodium borohydride was added and the reaction mixture was stirred for 3.5 hours. The solvents were removed in vacuo, and the residue was dissolved in water (3 ml) and the pH adjusted to 3.0 with 1N HCl. This was purified by reverse-phase chromatography on MCI gel CHP20P (37-75μ). eluting with water to yield 45.2 mg of the title compound as a white solid.

What is claimed is:

1. $N^2$-[N-(N-acetylmuramoyl)-L-alanyl]-N-(5,6-diamino-1-carboxy-6-oxohexyl)-D-α-glutamine.

2. $N^2$-[N-(N-acetylmuramoyl)-L-alanyl]-N-[5,6-diamino-1-[[1-[(1-carboxyethyl)carbamoyl]ethyl]-carbamoyl]-6-oxohexyl]-D-α-glutamine.

3. EM5556C, or a salt thereof, having the molecular formula $C_{32}H_{55}N_8O_{17}$, the sodium salt of which has the infrared spectrum in potassium bromide as shown in FIG. 1; and the sodium salt of which has the 400 MHz $^1$H NMR spectrum in deuterated water as shown in FIG. 2.

4. 2-(Acetylamino)-3-O-[(R)-2-[(S)-2-[[(R)-1-carboxy-4-[[(1S,5R)-5,6-diamino-1-carboxy-6-oxohexyl]amino]-4-oxobutyl]amino]-1-methyl-2-oxoethyl]-1-methyl-2-oxoethyl]-2-desoxy-D-glucitol.

* * * * *

UNITED STATES PATENT AND TRADEMARK OFFICE
CERTIFICATE OF CORRECTION

PATENT NO. : 4,474,693
DATED : October 2, 1984
INVENTOR(S) : Puspha Singh et al.

It is certified that error appears in the above—identified patent and that said Letters Patent is hereby corrected as shown below:

In the Abstract, line 2, "carboxyl" should be
--carboxy--.

In column 1, line 35, delete the second occurrence of the word "glutamine"; line 35 should read --diamino-1-carboxy-6-oxohexyl)-D-α-glutamine--.

The title of Example 2 should read: --2-(Acetylamino)-3-O-[(R)-2-[(S)-2-[[(R)-1-carboxy-4-[[(1S,5R)-5,6-diamino-1-carboxy-6-oxohexyl]amino]-4-oxobutyl]amino]-1-methyl-2-oxoethyl]-2-desoxy-D-glucitol--.

Signed and Sealed this

Twelfth Day of March 1985

[SEAL]

Attest:

DONALD J. QUIGG

Attesting Officer     Acting Commissioner of Patents and Trademarks